United States Patent [19]
Copeland et al.

[11] Patent Number: 6,130,743
[45] Date of Patent: Oct. 10, 2000

[54] COLORIMETRIC RED BLOOD CELL SENSOR

[75] Inventors: Hugh D. Copeland, Chula Vista; Gary F. Mastny; Andrew E. Patterson, both of San Diego, all of Calif.

[73] Assignee: The United States of America as represented by the Secretary of the Navy, Washington, D.C.

[21] Appl. No.: 09/340,377

[22] Filed: Jun. 28, 1999

[51] Int. Cl.$^7$ ................................................... G01N 33/48
[52] U.S. Cl. ................................................ 356/39; 356/410
[58] Field of Search ...................................... 356/39, 410

[56] References Cited

U.S. PATENT DOCUMENTS

| | | |
|---|---|---|
| 3,560,754 | 2/1971 | Kamentsky ............................. 250/218 |
| 3,910,701 | 10/1975 | Henderson et al. . |
| 3,969,024 | 7/1976 | Hashizume et al. . |
| 4,175,859 | 11/1979 | Hashizume et al. . |
| 4,819,752 | 4/1989 | Zelin . |
| 4,911,549 | 3/1990 | Karkar . |
| 4,925,299 | 5/1990 | Meisberger et al. . |
| 5,353,790 | 10/1994 | Jacques et al. . |
| 5,355,880 | 10/1994 | Thomas et al. . |
| 5,499,627 | 3/1996 | Steuer et al. . |
| 5,565,976 | 10/1996 | Fieggen et al. . |
| 5,647,359 | 7/1997 | Kohno et al. . |
| 5,682,038 | 10/1997 | Hoffman . |
| 5,734,464 | 3/1998 | Gibbs ........................................ 356/39 |
| 5,766,125 | 6/1998 | Aoyagi et al. . |
| 5,782,756 | 7/1998 | Mannheimer . |
| 5,936,714 | 8/1999 | Gibbs ........................................ 356/39 |

*Primary Examiner*—Robert Kim
*Assistant Examiner*—Philip Natividad
*Attorney, Agent, or Firm*—Harvey Fendelman; Peter A. Lipovsky; Michael A. Kagan

[57] ABSTRACT

A colorimetric red blood cell sensor provides an automatic system for detecting and preventing the further mixing of red blood cells and plasma. The sensor includes a processor that controls blue and red light sources so that they collectively generate pulsed blue and red light signals that are directed through blood serum held in an optically transparent container. The red and blue signals are 180 degrees out of phase, and hence staggered, with respect to each other. A photodetector system detects the pulsed red and blue light signals and generates output signals representing the intensities of the staggered signals received by the photodetector system. A microprocessor determines the ratio of the intensities of the red and blue light signals detected by the photodetector system. If the ratio exceeds a limit, the microprocessor generates a fluid control signal that prevents further mixing of red blood cells and plasma.

9 Claims, 2 Drawing Sheets

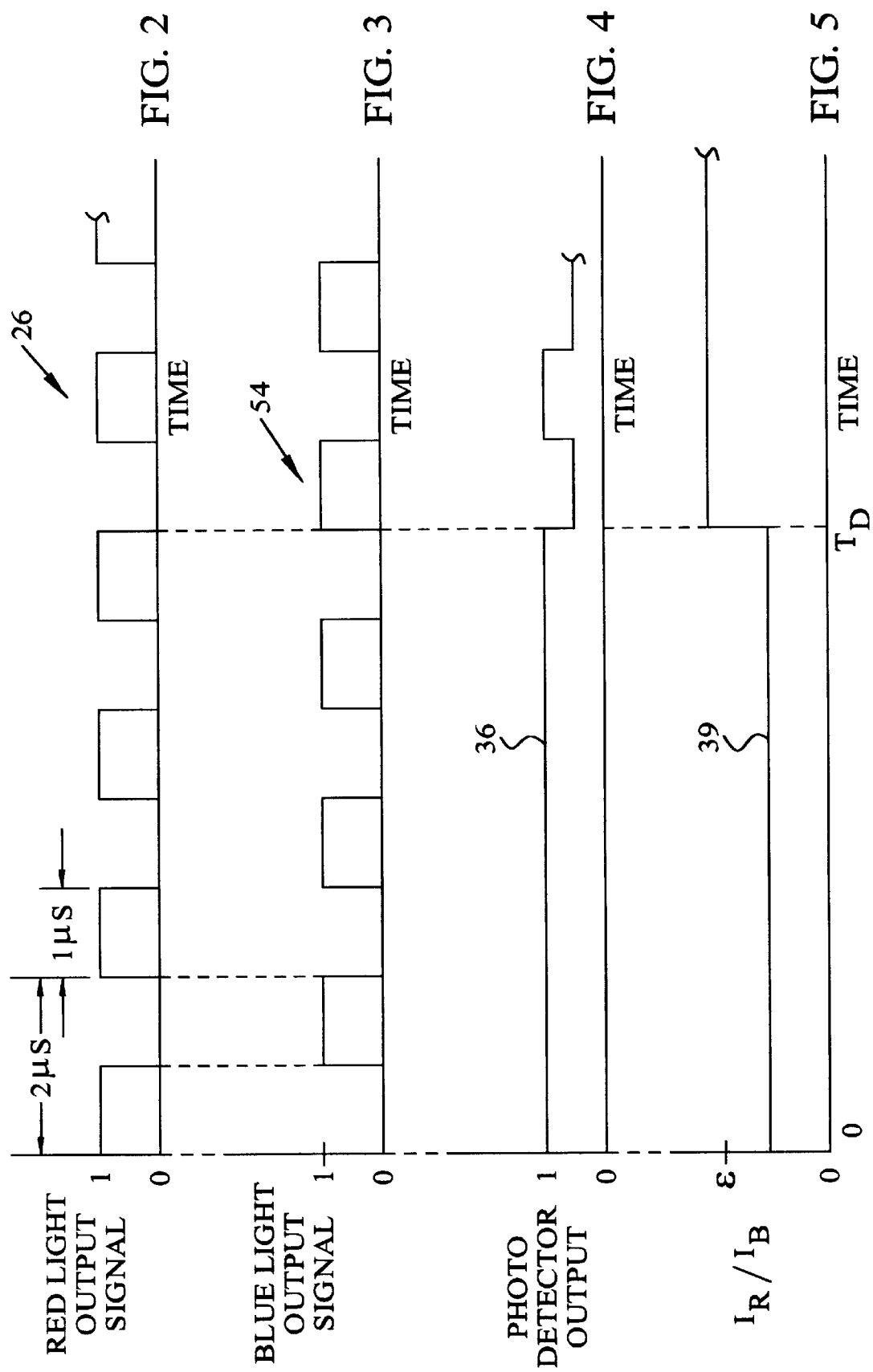

COLORIMETRIC RED BLOOD CELL SENSOR

BACKGROUND OF THE INVENTION

The present invention generally relates to a sensor for detecting red blood cells in plasma by comparing the absorption of red light and blue light directed through the plasma.

Blood generally consists of red and white blood cells suspended in plasma. Red blood cells find widespread use for making up serious blood losses as may be incurred during operations or as a result of injury. In order to assure adequate blood supplies for such contingencies, hospital blood banks and the military store red blood cells. In the process for separating red blood cells from plasma and other blood products, blood is typically placed in a flexible bag that is spun in a centrifuge. After being centrifuged, the red blood cells, white blood cells, and plasma are grouped in layers. The plasma and white blood cells have a lower density than the red blood cells so the white blood cells and plasma collect in layers above the red blood cells that are at the bottom of the bag. The bag then is squeezed so that the white blood cells and plasma are "expressed" out of the bag whereupon mainly red blood cells remain. Such separation currently is done under human supervision. When the operator observes red blood cells at a certain point in the bag, the operator stops the process. The result is a donor bag containing red blood cells with a small amount of plasma, and red blood cell free plasma in a second bag. The red blood cells may then be stored for near term use or prepared for cryopreservation for long term storage and later use.

It is standard blood bank procedure to separate red blood cells from plasma. Such separation makes available to the patient only those blood components required, whether it is the oxygen transport provided by the red blood cells, or the volume effects provided by the plasma. Red blood cells carry antibodies that may cause transfusion reactions in patients not properly cross-matched. Plasma from several donors is typically administered to a single patient. Foreign red blood cells may result in harmful hemolytic transfusion reactions such as hemolysis, anaphyltic reactions, urtcaria, noncardic pulmonary edema, hepatitis, and alloimmunization to red blood cell or white blood cell antigens, platelets or plasma proteins, etc. Thus, it is not desirable for plasma to contain red blood cells. Therefore, it is important that red blood cells plasma be separated as much as possible from plasma.

SUMMARY OF THE INVENTION

A colorimetric red blood cell sensor provides an automatic system for detecting red blood cells in plasma, and may be further used to prevent the further mixing of red blood cells in plasma during blood component separation. The sensor includes a processor that controls blue and red light sources so that they sequentially generate pulsed blue and red light signals that are directed through blood components held in or passing through an optically transparent container. The red and blue signals are 180 degrees out of phase, and hence staggered over time, with respect to each other. A photodetector system detects the pulsed red and blue light signals and generates output signals representing the intensities of the staggered signals received by the photodetector system. A microprocessor determines the ratio of the intensities of the red and blue light signals detected by the photodetector system. If the ratio exceeds a limit, the microprocessor generates a fluid control signal that prevents further mixing of red blood cells and plasma.

In the preferred embodiment, the red and blue light sources may be implemented as red and blue light emitting diodes, respectively. These and other advantages of the invention will become more apparent upon review of the accompanying drawings and specification, including the claims.

BRIEF DESCRIPTION OF THE DRAWINGS

FIG. 2 is a timing diagram of the light output of the red photodiode of FIG. 1.

FIG. 3 is a timing diagram of the light output of the blue photodiode of FIG. 1.

FIG. 4 is a representative timing diagram of output of the photodetector of FIG. 1 under steady-state conditions.

FIG. 5 is a diagram illustrating the ratio of red to blue light when red blood cells are detected in plasma.

Throughout the several views, like elements are referenced using like references.

DESCRIPTION OF THE PREFERRED EMBODIMENT

Figure 1:
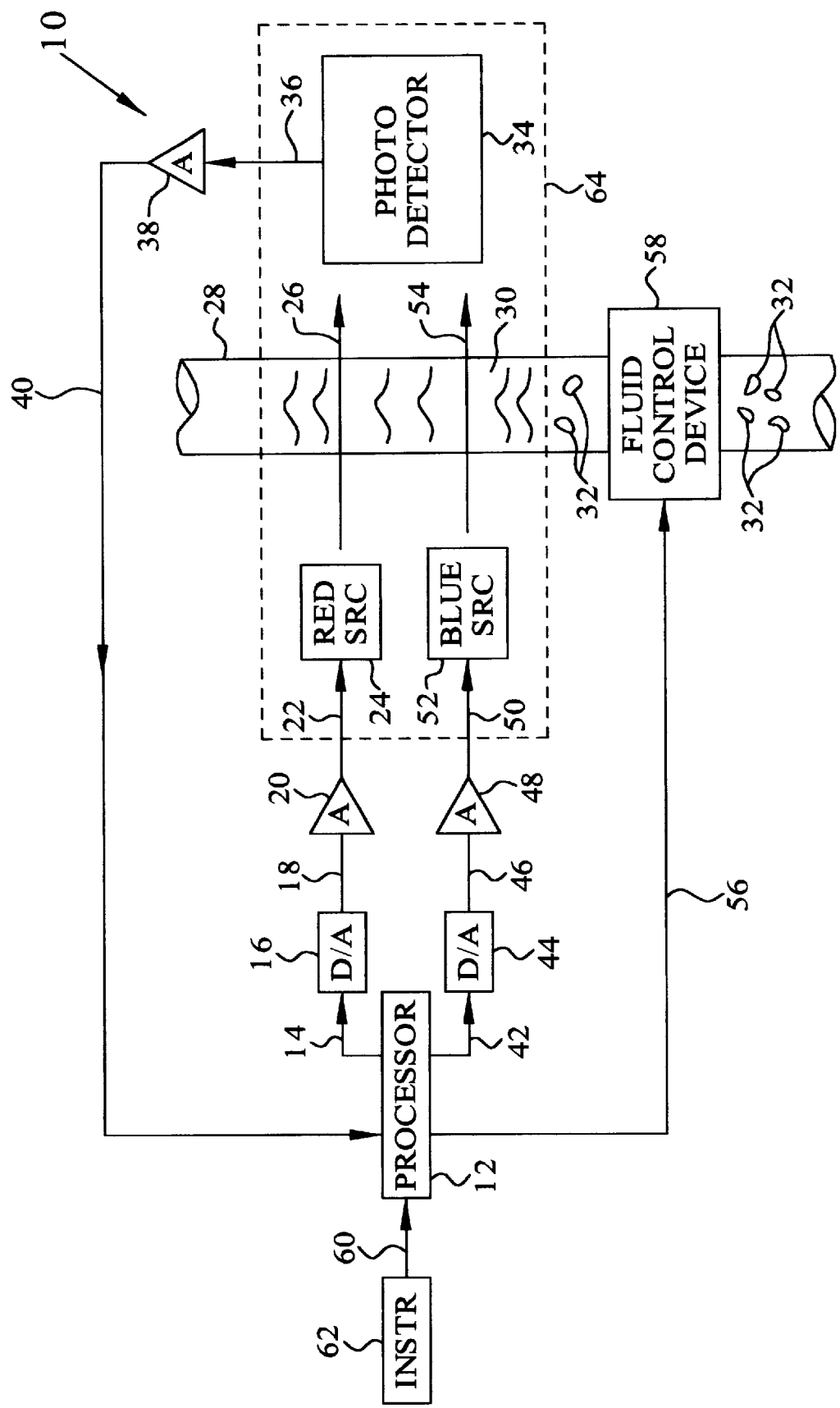
FIG. 1 illustrates a block diagram of a colorimetric red blood cell sensor system for detecting red blood cells in plasma that embodies various features of the present invention.

The present invention is directed to a colorimetric red blood cell sensor 10 for detecting the presence of red blood cells in plasma. Referring to FIG. 1, sensor 10 includes a processor 12 that generates a pulsed digital red light control output signal 14 that is transformed by digital to analog converter 16 into analog red light control signal 18. By way of example, digital red light control output signal 14 may have a period of 2 milliseconds and a pulse width of 1 milliseconds. Referring again to FIG. 1, analog red light control signal 18 is transformed by amplifier 20 into an amplified red light control signal 22 that is provided to excite red light source 24. Upon receiving amplified red light control signal 22, red light source 24 generates red light output signal 26 as a series of pulses having a pulse period of about 2 milliseconds and a pulse width of about 1 milliseconds, as shown in FIG. 2. Red light output signal 26 has a waveform substantially identical to the waveform of digital red light control output signal 14 (not shown). Red light output signal 26 is directed through plasma 30 that may include red blood cells 32. Plasma 30 and any red blood cells 32 are contained within an optically transparent fluid container 28, such as a tube.

Similarly, processor 12 generates a pulsed digital blue light control output signal 42 that is transformed by digital to analog converter 44 into analog blue light control signal 46. By way of example, digital blue light control output signal 42 may have a period and pulse width that are substantially identical to those of digital red light control output signal 14, however, signals 14 and 42 preferably are 180 degrees out of phase with respect to one another such that the pulses of signals 14 and 42 are staggered with respect to each other. Referring again to FIG. 1, analog blue light control signal 18 is transformed by amplifier 48 into an amplified blue light control signal 50 that is provided to excite blue light source 52. Upon receiving amplified blue light control signal 22, blue light source 24 generates blue light output signal 26 as a series of pulses having a pulse period of about 2 milliseconds and a pulse width of about 1 milliseconds, as shown in FIG. 3. Blue light output signal 26 is directed through plasma 30 that may include red blood cells 32. Blue light output signal 54 has a waveform substantially identical to the waveform of digital blue light control output signal 42 (not shown). Thus it may be appreciated that red and blue light signals 26 and 54 are staggered with respect to each other as an alternating series of pulsed red and blue light signals. Red and blue light sources 24 and 52 preferably are implemented as red and blue light emitting diodes, respectively.

Photodetector 34, such as a phototransistor, is positioned to receive light signals 26 and 54, and generate a pulsed output signal 36 that represents the intensities of both signals 26 and 54 as detected by photodetector 34. A timing diagram of signal 36 is shown in FIG. 4. In FIG. 4, the output signal 36 of photodetector 34 is essentially constant from time t=0 to time $t=T_D$, where t represents time and $T_D$ represents a time at which red blood cells are first detected in plasma 30. While red and blue light signals 26 and 54, respectively, transect plasma 30 without passing through any red blood cells, the output signal 36, which is the vector sum of signals 26 and 54, remains essentially constant. As shown in FIG. 2, red light signal 26, centered about 650 nm, is negligibly attenuated as it passes through red blood cells. However, as shown in FIG. 3, blue light signal 54 is significantly attenuated about a center wavelength of 420 nm as it passes through red blood cells. The different responses red blood cells impose on red and blue light are used to determine the presence of red blood cells in plasma 30. Thus, as shown in FIG. 5, the ratio 39 of red light signal 26 and to blue light signal 54 ($I_R/I_B$) as detected by photodetector 34 as a function of time, which is generally constant from t=0 to $t=T_D$, increases significantly from $t=T_D$ and later when light signals 26 and 54 transect red blood cells 32.

Signal 36 is amplified by amplifier 38 and transformed into amplified output signal 40. Processor 40 has an internal clock (not shown) which times the sampling of signal 36 so that from signal 36, processor 40 determines the intensities of red and blue light signals 26 and 54 detected by photodetector 34. Processor 12 compares the ratio $I_R/I_B$, where $I_R$ represents the intensity of red light signal 26 as detected by photodetector 34, and $I_B$ represents the intensity of blue light signal 54 as detected by photodetector 34. If $I_R/I_B > \epsilon$, where $\epsilon$ represents a predetermined threshold value, then processor 40 determines that red blood cells 32 are present in plasma 30 between the red and blue light sources 24 and 52, respectively, and photodetector 34. In such case, processor 12 generates a fluid control signal 56 that is provided to fluid control device 58, causing the fluid control device 58 to change state and thereby prevent additional red blood cells from flowing between the light sources 24 and 52, and photodetector 34. As exemplified in FIG. 5, $I_R/I_B > \epsilon$ at $T_D$ and afterwards.

By way of example, fluid control device 58 may be a valve or a pump such as a plasma express pump. When processor 12 receives a START instruction 60 via input device 62, processor 12 generates a fluid control signal 56 having a characteristic which changes the state of fluid control device 58 so that fluid 30 may pass between light sources 24 and 52, and photodetector 34, that collectively may be referenced as sensor head 64.

Obviously, many modifications and variations of the present invention are possible in light of the above teachings. It is therefore to be understood that within the scope of the appended claims, the invention may be practiced otherwise than as specifically described.

We claim:

1. A colorimetric red blood cell sensor, comprising:
   a tube for conveying blood plasma;
   a red light source for generating a pulsed red light signal that is directed through said tube;
   a blue light source for generating a pulsed blue light signal that is directed through said tube, where said pulsed blue light signal is about 180 degrees out of phase with respect to said pulsed red light signal;
   a photodetector system, positioned such that said tube is interposed between said red and blue light sources and said photodetector system, for detecting the intensities of said red light signal and said blue light signal, and for generating a first output signal alternately representing the intensities of said red and blue light signals detected by said photodetector; and
   a processor for implementing processor functions in response to receiving said first output signal from said photodetector, where said processor functions include: a) determining the value of the ratio of $I_R/I_B$, where $I_R$ represents said intensity of said pulsed red light signal detected by said photodetector and $I^B$ represents said intensity of said pulsed blue light signal detected by said photodetector; and b) generating a second output signal when $I_R/I_B > \epsilon$, where $\epsilon$ represents a limit.

2. The colorimetric red blood cell sensor of claim 1 wherein;
   said red light source is a first light emitting diode for generating said pulsed red light signal; and
   said blue light source is a second light emitting diode for generating said pulsed blue light signal.

3. The colorimetric red blood cell sensor of claim 1 further including a fluid control device which changes state in response to receiving said second output signal.

4. The colorimetric red blood cell sensor of claim 1 wherein said processor functions further include a) generating a third output signal for causing said red light source to generate said pulsed red light signal; and b) generating a fourth output signal for causing said blue light source to generate said pulsed blue light signal.

5. A colorimetric red blood cell sensor, comprising:
   a tube for conveying blood plasma;
   a fluid control device having a first state in which said blood plasma flows through said fluid control device and a second non-flow state;
   a red light source for generating a pulsed red light signal that is directed through said tube;
   a blue light source for generating a pulsed blue light signal that is directed through said tube, where said pulsed red and blue light signals are approximately 180 degrees out of phase with respect to each other;
   a photodetector system, positioned such that said tube is interposed between said red and blue light sources and said photodetector system, for detecting the intensities of said pulsed red light signal and said pulsed blue light signal that have propagated through said blood plasma, and for generating a first output signal alternately representing the intensities of said pulsed red light signal and pulsed blue light signal detected by said photodetector; and
   a processor for implementing processor functions in response to receiving said first output signal from said photodetector, where said processor functions include: a) determining the value of the ratio of $I_R/I^B$, where $I_R$ represents the intensity of said pulsed red light signal detected by said photodetector and $I^B$ represents the intensity of said pulsed blue light signal detected by said photodetector; and b) generating a fluid control output signal for switching said fluid control device between said first and second states when $I_R/I_B > \epsilon$, where $\epsilon$ represents a limit.

6. The colorimetric red blood cell sensor of claim 5 wherein;

said red light source is a first light emitting diode for generating said pulsed red light signal; and said blue light source is a second light emitting diode for generating said pulsed blue light signal.

7. The colorimetric red blood cell sensor of claim 5 wherein said fluid control device is a pump.

8. The colorimetric red blood cell sensor of claim 5 wherein said fluid control device is a valve.

9. The colorimetric red blood cell sensor of claim 5 wherein said processor functions further include: a) generating a third output signal for causing said red light source to generate said pulsed red light signal; and b) generating a fourth output signal for causing said blue light source to generate said pulsed blue light signal.

* * * * *